US009993777B2

(12) United States Patent
Hayashi et al.

(10) Patent No.: US 9,993,777 B2
(45) Date of Patent: Jun. 12, 2018

(54) POROUS MEMBRANE, BLOOD PURIFYING MODULE INCORPORATING POROUS MEMBRANE, AND METHOD FOR PRODUCING POROUS MEMBRANE

(71) Applicant: TORAY INDUSTRIES, INC., Tokyo (JP)

(72) Inventors: Akihiro Hayashi, Otsu (JP); Shiro Nosaka, Otsu (JP); Yoshiyuki Ueno, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 121 days.

(21) Appl. No.: 14/913,919

(22) PCT Filed: Sep. 26, 2014

(86) PCT No.: PCT/JP2014/075591
§ 371 (c)(1),
(2) Date: Feb. 23, 2016

(87) PCT Pub. No.: WO2015/046411
PCT Pub. Date: Apr. 2, 2015

(65) Prior Publication Data

US 2016/0220965 A1 Aug. 4, 2016

(30) Foreign Application Priority Data

Sep. 30, 2013 (JP) ................................ 2013-203827

(51) Int. Cl.
*B01D 67/00* (2006.01)
*B01D 69/02* (2006.01)
(Continued)

(52) U.S. Cl.
CPC .......... *B01D 67/0013* (2013.01); *A61M 1/16* (2013.01); *B01D 63/02* (2013.01);
(Continued)

(58) Field of Classification Search
CPC . A61M 1/16; B01D 2323/02; B01D 2325/02; B01D 2325/36; B01D 63/02;
(Continued)

(56) References Cited

FOREIGN PATENT DOCUMENTS

| | | | |
|---|---|---|---|
| JP | 58-114702 | A | 7/1983 |
| JP | 61-93801 | A | 5/1986 |
| JP | 2005-349093 | A | 12/2005 |

OTHER PUBLICATIONS

International Search Report issued in PCT/JP2014/075591 dated Dec. 22, 2014.

(Continued)

*Primary Examiner* — Dirk Bass
(74) *Attorney, Agent, or Firm* — Birch, Stewart, Kolasch & Birch, LLP

(57) ABSTRACT

The purpose of the present invention is to provide a porous membrane that has both high water permeability and excellent protein fractionation performance. Provided is a method for producing a porous membrane, said method comprising a step for discharging a membrane-forming dope that contains a hydrophilic polymer from a slit formed in a mouthpiece, and a step for, after the passage of the discharged membrane-forming dope through a dry part, solidifying the membrane-forming dope in a coagulation bath to give a porous membrane, wherein the cross-section area of the slit is 3-30 times inclusive as large as the cross-section area of the solidified porous membrane.

14 Claims, 3 Drawing Sheets

(51) Int. Cl.

| | |
|---|---|
| ***A61M 1/16*** | (2006.01) |
| ***B01D 71/58*** | (2006.01) |
| ***B01D 71/68*** | (2006.01) |
| ***B01D 69/08*** | (2006.01) |
| ***B01D 63/02*** | (2006.01) |

(52) U.S. Cl.
CPC ......... *B01D 67/0016* (2013.01); *B01D 69/02* (2013.01); *B01D 69/08* (2013.01); *B01D 71/58* (2013.01); *B01D 71/68* (2013.01); *B01D 2323/02* (2013.01); *B01D 2325/02* (2013.01); *B01D 2325/36* (2013.01)

(58) Field of Classification Search
CPC ....................... B01D 67/0013; B01D 67/0016; B01D 69/02; B01D 69/08; B01D 71/58; B01D 71/68
See application file for complete search history.

(56) References Cited

OTHER PUBLICATIONS

Written Opinion of the International Searching Authority issued in PCT/JP2014/075591 dated Dec. 22, 2014.

POROUS MEMBRANE, BLOOD PURIFYING MODULE INCORPORATING POROUS MEMBRANE, AND METHOD FOR PRODUCING POROUS MEMBRANE

TECHNICAL FIELD

This invention relates to a porous membrane, a blood purifying module incorporating the porous membrane, and a method for producing porous membrane. More specifically, this invention relates to a porous membrane used for an artificial kidney.

BACKGROUND ART

Porous membranes are suitable for use in membrane separation of substances in a liquid wherein the substance is sieved depending on the pore size. Porous membranes are widely used in medical applications such as hemodialysis and hemofiltration as well as water treatment such as those by household water purifier and water purification.

In particular, in the field of blood purification such as hemodialysis, there is a demand for a separation membrane having a high fractionation performance capable of selectively allowing the permeation of the unnecessary low and medium molecular weight substances in the blood while not allowing the permeation of the necessary high molecular weight substance. Typical low molecular weight substances include uremic toxins such as urea, creatinine, and phosphorus. In the dialysis, these substances are mainly removed by diffusion, and therefore, the separation membrane is required to be highly water permeability. Typical medium molecular weight substances include $\beta_2$-microglobulin. $\beta_2$-microglobulin is a protein having a molecular weight of about 12,000, which is conceivably a substance responsible for dialysis-related amyloidosis, and accordingly, removal of this substance in the dialysis is required. On the other hand, albumin which is a protein having a molecular weight of about 66,000 fulfills the functions including maintenance of the osmotic pressure and retention and transportation of various substances. Accordingly it is a substance required to remain in the blood and its loss in the dialysis should be suppressed. Recently, it is considered that some substances with the molecular weight in the range of near 30,000 as typically represented by $\alpha_1$-microglobulin are also subject to the removal.

Accordingly, there is a demand for a porous membrane simultaneously exhibiting a high water permeability and a high protein fractionation performance which can be used as a separation membrane for the dialysis. In particular, in the hemodiafiltration which is a therapy recently receiving attention wherein blood which has been diluted with dialysis solution is concentrated by filtration through the separation membrane, the separation membrane used for the hemodiafiltration is required to have a high water permeability. Also required is a high protein fractionation performance so that the $\alpha_1$-microglobulin having a high molecular weight can be removed at a high degree while suppressing the loss of albumin.

When the pore diameter of the porous membrane is reduced to suppress the loss of albumin, water permeability will become reduced and ability of removing low molecular weight substances such as uremic toxins will also be reduced. On the other hand, when the pore diameter of the porous membrane is increased to improve the ability of removing the $\beta_2$-microglobulin, amount of the albumin lost will be increased despite the improvement in the water permeability. As described above, the water permeability and the protein fractionation performance are greatly affected by the pore diameter on the surface of the porous membrane, and simultaneous realization of the water permeability and the protein fractionation performance has been difficult.

An exemplary technique for improving the water permeability and the fractionation performance of the porous membrane is the one wherein the major diameter is increased in relation to the minor diameter by stretching the surface pores. The method used for stretching the pores on the surface of the porous membrane include a method wherein the stretching is conducted after the solidification of the porous membrane and a method wherein drafting is conducted before the solidification of the porous membrane.

Patent Documents 1 and 2 disclose the porous membranes produced by the stretching. Patent Documents 3 and 4 disclose the porous membranes produced by the drafting. Patent Documents 5 and 6 disclose the porous membranes wherein stretched shape of the pores on the inner surface have been formed by adjusting the composition of the spinning dope solution and membrane forming temperature to thereby control the pore development and coagulation by the phase separation.

PRIOR ART DOCUMENTS

Patent Documents

Patent Document 1: Japanese Unexamined Patent Publication (Kokai) No. SHO 64-75015

Patent Document 2: Japanese Unexamined Patent Publication (Kokai) No. SHO 59-64055

Patent Document 3: International Publication WO 2010/029908

Patent Document 4: Japanese Unexamined Patent Publication (Kokai) No. HEI 6-165926

Patent Document 5: Japanese Unexamined Patent Publication (Kokai) No. SHO 58-114702

Patent Document 6: Japanese Unexamined Patent Publication (Kokai) No. HEI 9-308685

SUMMARY OF THE INVENTION

Problems to be Solved by the Invention

Patent Document 1 discloses a porous membrane wherein the major diameter of the surface pores has been elongated to at least 1.5 times the minor diameter of the surface pores by stretching. However, the pore minor diameter is as large as 3 μm to 30 μm, and this membrane is incapable conducting the protein fractionation. In addition, this document is silent about the dispersion of the major diameter. Patent Document 2 discloses a porous membrane for blood treatment wherein the major diameter of the surface pores has been elongated to 1.5 to 20 times the minor diameter of the surface pores by stretching. This document, however, is silent about the range of the minor diameter of the surface pores, and this document is also silent about the dispersion of the major and minor diameter which contributes for the fractionation performance.

Patent Document 3 discloses a hollow fiber membrane for water purifiers wherein the pores formed by drafting have a high ratio of the major diameter to the minor diameter as well as high porosity. However, this hollow fiber membrane is incapable of conducting the protein fractionation due to the large minor diameter of the surface pore of 1 μm. Despite the assumed relatively high dispersion of the pore diameter, this document is silent on this improvement. This document is also silent on the residual amount of the hydrophilic polymer which is necessary for the improvement of the water permeability and the biocompatibility. Patent Document 4 discloses a porous membrane wherein the minor diameter of the surface pores is 1 nm to 50 nm, and this document also discloses the spinning at a sufficiently high draft ratio. However, this document is silent on the ratio of the major diameter to the minor diameter, and it should be noted that the ratio of the major diameter to the minor diameter does not automatically increase with the increase in the draft ratio as will be described below. This document is also silent on the dispersion of the pore diameter which contributes for the fractionation performance. Note that this document is also silent on the major diameter of the surface pores.

Patent Document 5 discloses a hollow fiber membrane having an inner surface wherein average minor diameter is up to 50 nm and the ratio of the major diameter to the minor diameter is at least 3. The document also disclose that the minor diameter of the pores should be as consistent as possible. However, the document does not disclose any means for achieving such uniformity, and the document does not even disclose stretching or drafting for the elongation of the surface pores. Accordingly, precise control of the dispersion of the pore diameter is not realized in this document, and high fractionation performance cannot be expected. It is to be noted that this membrane suffers from an increased permeation resistance due to the relatively small pore diameter on the outer surface, and improvement of the water permeability is difficult. Patent Document 6 discloses a porous membrane wherein major diameter of the surface pores is at least 2 times, and preferably at least 3 times larger than the minor diameter and the lower limit of the minor diameter of the pores is 20 nm. This document discloses that "the average width of less than 0.02 μm results in a reduced water permeation speed and reduced ultrafiltration speed in the blood filtration, and also, in the increased risk of clogging with lapse of time with reduced permeability of the uremic toxin such as urea and creatinine. More preferable lower limit of the average width is 0.04 μm", and the document does not consider the ratio of the major diameter to the minor diameter of the pores or the dispersion of the pore diameter in the range of the pore minor diameter of the present invention. With regard to the minor diameter of the surface pores, the document disclose that the minor diameter of the surface pores is preferably consistent for the realization of a stable fractionating property, while the document is utterly silent for the particular means such as stretching or drafting for the elongation of the surface pores, and therefore, it is very likely that the dispersion of the major diameter and the minor diameter of the pores are not precisely controlled in the document.

An object of the present invention is to provide a porous membrane simultaneously exhibiting a high water permeability and a high fractionation performance.

Means for Solving the Problems

In order to solve the problems as described above, the present invention has the following constitution.

Accordingly, the present invention provides a porous membrane used for blood purification containing a hydrophilic polymer at a content of at least 0.5% by weight and up to 8% by weight wherein pores formed on one surface satisfy the following (A) and (B):

(A) average of ratio of the major diameter to the minor diameter of the pores is at least 3, and (B) average of the minor diameter is at least 5 nm and up to 20 nm and a standard deviation is up to 4 nm.

While the measurement of the pore diameters will be described later, in another preferable embodiment of the present invention, pores formed on the other surface satisfy the following (C) and (D):

(C) average of ratio of the major diameter to the minor diameter of the pores is at least 1.5, and (D) average of the minor diameter is at least 0.2 μm and up to 0.6 μm.

More specifically, the pores formed on one surface satisfy the (A) and (B) while the pores formed on the other surface satisfy the (C) and (D). In the more preferably embodiment of the present invention, the porous membrane is a hollow fiber membrane, and in the still more preferably embodiment, in the hollow fiber membrane, the surface satisfying the (A) and (B) is the inner surface, and the surface satisfying the (C) and (D) is the outer surface. When used for blood-purification purpose, the blood passes in the interior of the membrane, and the unnecessary components of the blood is removed in the direction from the inner surface having the pores with more minute diameters to the outer surface having the pores with the relatively large diameters.

According to another preferable embodiment of the present invention, the surface having the pores satisfying the (A) and (B) has a porosity of at least 1% and up to 10%.

According to a preferable embodiment of the present invention, material constituting main component of the porous membrane is an amorphous polymer, and according to further preferable embodiment of the present invention, the amorphous polymer is a polysulfone polymer. The main component is a component having the highest weight content in the membrane.

According to another aspect of the present invention, the present invention provides a module for blood purification accommodating the porous membrane as described above.

Advantageous Effect of the Invention

The present invention provides a porous membrane simultaneously exhibiting high water permeability and high fractionation performance. For example, when such porous membrane is used as a hollow fiber membrane for blood purification, and in particular, for an artificial kidney, the resulting module will exhibit high ability of removing low molecular weight substances such as uremic toxin and high fractionation performance allowing passage of low molecular weight proteins such as $\mu_2$-microglobulin while avoiding passage of medium molecular weight proteins such as albumin.

DESCRIPTION OF PREFERRED EMBODIMENTS

Figure 1:
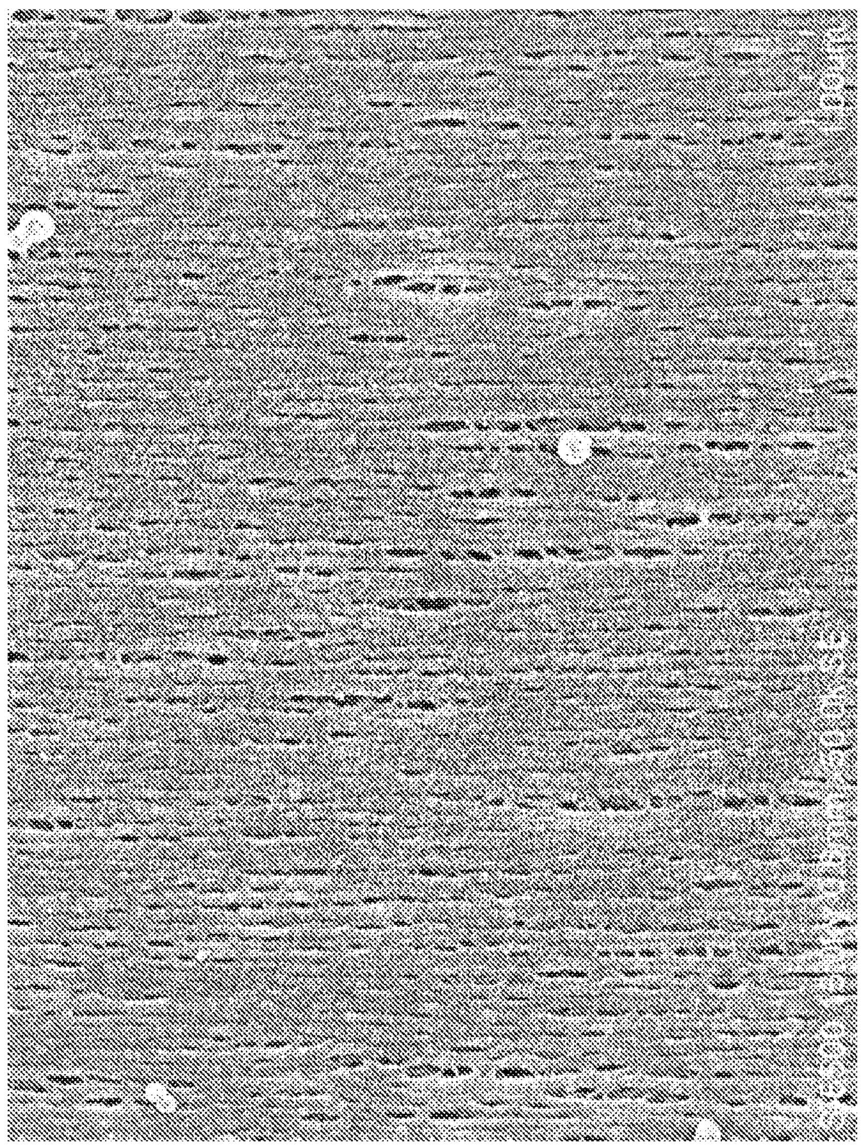
FIG. 1 is a picture of the surface of the porous membrane produced by the method of the Example 1 taken by a scanning electron microscope (SEM).
Figure 2:
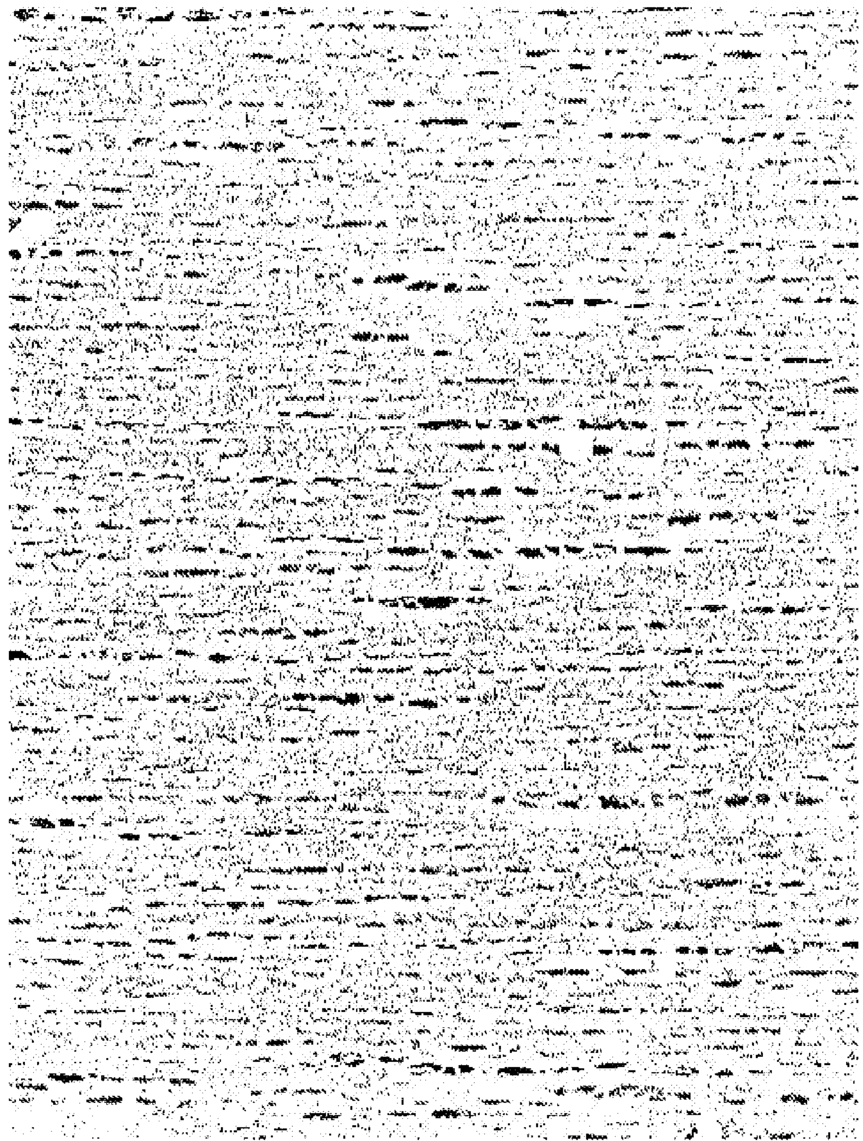
FIG. 2 is a picture prepared by binarizing the SEM picture of FIG. 1.
Figure 3:
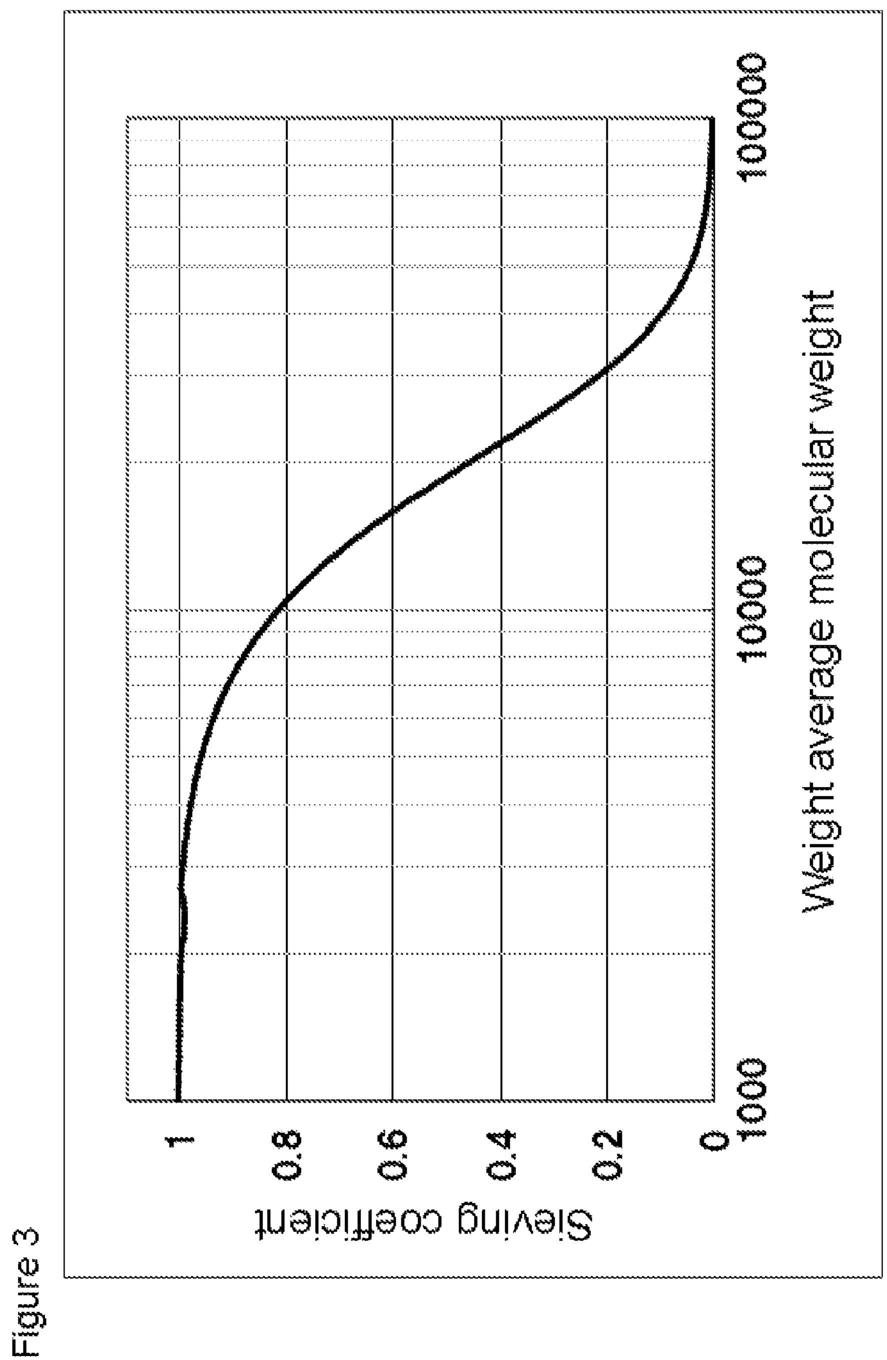
FIG. 3 is a graph showing the dextran fractionation curve.

Porous membranes generally accomplish their function of sieving the substance to be removed by the size of the pores on the surface, and therefore, when the pores on the membrane surface has an oblong shape with the major and minor axis directions, the fractionation performance depends on the minor diameter of the surface pores. For example, when the porous membrane is a hollow fiber membrane, the pores are stretched in the course of spinning in the axial direction since the dope solution undergoing the solidification is stretched in the axial direction, and accordingly, the axial direction of the hollow fiber membrane corresponds to the major axis of the pores, and the diameter in the direction perpendicular to the axial direction is the minor diameter. In the sieving by the pore size, apparent size of the substance to be removed is larger than the actual size due to the effect of Brownian movement and the like, and therefore, the surface pore diameter should be larger than the size of the substance to be removed. In consideration of this, when the porous membrane according to the present invention is used as a hollow fiber membrane for blood purification application, for example, in the dialysis, average of the minor diameter of the pores on one surface of the membrane (the surface having the fractionating function, usually the inner surface in the case of the hollow fiber membrane) is typically at least 5 nm, preferably at least 7 nm, and still more preferably at least 10 nm in order to remove the $\beta_2$-microglobulin since molecular size of the $\beta_2$-microglobulin which is the substance to be removed is about 3 nm. The minor diameter of the pores on such surface of less than 5 nm is undesirable since the water permeability greatly reduces in such diameter range. On the other hand, albumin which is preferably left unremoved in the dialysis has a molecular size of about 8 nm, and the pore minor diameter on the surface as described above typically has an average of up to 20 nm, preferably up to 18 nm, more preferably up to 15 nm, and still more preferably up to 12 nm in order to prevent the permeation of the albumin. The separation of the proteins to be removed and the proteins not to be removed can be improved by controlling the pore minor diameter as described above.

In order to improve the fractionation performance of the protein, consideration of not only the average but also dispersion of the minor diameter of the pores on that surface is necessary. In the present invention, the standard deviation which represents the dispersion of the minor diameter of the pore on the surface is typically up to 4 nm, preferably up to 3.8 nm, and still more preferably up to 3.5 nm. On the other hand, adequate standard deviation is at least 2 nm in view of the difficulty in controlling the pore diameter, and realization is easier when the standard deviation is at least 2.5 nm. The dispersion in the surface pore diameter can be effectively reduced by stretching the pores on the surface in the direction of major diameter. For example, in the case of a hollow fiber membrane, circular pores are stretched when the hollow fiber membrane is stretched in the axial direction, and the resulting oblong pores exhibit reduced dispersion of the pore minor diameter. When the pores on the surface are stretched in the direction of the major diameter, pores with large minor diameter undergo larger deformation, and as a consequence, minor diameter of larger holes is reduced to a larger degree compared with small holes wherein the minor diameter is not reduced so much. This results in the decrease of the minor diameter dispersion. With regard to the fractionation performance which will be described below, it can be calculated from the absolute value of slope of the fractionation curve depicted by plotting the values of dextran sieving coefficient for each molecular weight.

By increasing the major diameter of the pores on the surface while suppressing the change in the minor diameter, resistance of the water permeation can be reduced while retaining the fractionation performance, and improvement of the water permeability is thereby enabled, and the removal performance is also improved. In the dialysis, low molecular weight substances can be diffused to a higher degree when the membrane has higher water permeability. In other words, the water permeability will be increased in relation to the fractionation performance when the average of the ratio of the major diameter to the minor diameter of the pores (minor diameter/major diameter) is higher. Accordingly, the average of the ratio should be at least 3, and this average is preferably at least 3.5. In the meanwhile, strength of the membrane structure is also important, and in such view, the average of the ratio is preferably up to 6, and more preferably up to 4.

An effective method used for increasing the average of the ratio of the major diameter to the minor diameter of the pores on the surface as described above include stretching of the pores, and more specifically, stretching of the pores after the solidification of the porous membrane and stretching of the pores before the solidification of the porous membrane by increasing the draft ratio. Of these, the increase of the draft ratio is preferable in view of the wide applicability with no limitation on the material and the production method of the porous membrane. On the other hand, the stretching method can be used only when the porous membrane has sufficient strength, and use of this method is limited to the case, for example, when the membrane material used is a crystalline polymer or the like.

The draft ratio is the value obtained by dividing the take up speed of the porous membrane with the linear speed of ejection from the slit ejecting the spinning dope solution. The linear ejection speed is the value obtained by dividing the ejection flow rate with the cross-sectional area of the slit in the spinneret from which the dope solution is ejected. Accordingly, the draft ratio is usually increased by means of increasing the take up speed. In the present invention, however, the draft ratio is preferably increased by means of increasing the cross-sectional area of the ejection part of the slit. This method of increasing the cross-sectional area of the slit is preferable since this method is capable of readily accomplishing the increase in the draft ratio without changing the shape of the porous membrane. The method of increasing the take up speed is associated with the risk of losing the physical strength of the porous membrane due to the decrease in the cross-sectional area of the porous membrane. Mere increase in the take up speed may invite coagulation of the polymer in the coagulation bath before sufficient stretching of the pores in the axial direction of the membrane due to shorter time before entering of the membrane in the coagulation bath, and in such case, sufficient stretching of the pores is difficult by the increase in the draft ratio.

In the present invention, it has been found that, when a porous membrane having the same thickness is formed, the linear ejection speed can be reduced by increasing the ratio of the cross-sectional area of the slit formed in the spinneret for ejecting the spinning dope to the cross-sectional area of the film thickness part of each solidified porous membrane, and therefore, the draft ratio can be increased by without changing the take up speed to thereby stretch the surface pores. The ratio of the cross-sectional area of the slit to the cross-sectional area of the film thickness part of the porous membrane is preferably at least 3, more preferably at least 5, and still more preferably at least 10. On the other hand, an excessively high cross-sectional area ratio results in the difficulty of ejection control and fiber breakage and the like, and accordingly, the cross-sectional area ratio is preferably up to 30, and more preferably up to 20.

This applies not only for the case when the porous membrane is a hollow fiber membrane but also for the flat membrane and solid fiber membrane, and the surface pores are efficiently stretched by improving the draft ratio by increasing the spinneret slit cross-sectional area. The dispersion of the pore diameter is thereby reduced.

The major diameter of the pores on the surface satisfying such requirements (which is hereinafter referred to as the surface having the pores satisfying (A) and (B)) mainly contributes for the water permeability. Stretching of the holes results in the increase of the pore area, and this contributes for the improvement of the water permeability. Accordingly, average of the pore major diameter is preferably at least 25 nm, more preferably at least 30 nm, and even more preferably at least 35 nm. In the meanwhile, structural strength of the membrane will be insufficient when the average pore major diameter is too large, and therefore, the average pore major diameter is preferably up to 100 nm, more preferably up to 70 nm, and even more preferably up to 50 nm.

Since the pore major diameter is formed by the stretching of pores of various sizes formed during the phase separation, the dispersion of the pore major diameter is increased by the stretching. In view of the water permeability, the pore major diameter preferably has a greater dispersion, and accordingly, the standard deviation of the pore major diameter is preferably at least 10 nm, more preferably at least 13 nm, and still more preferably at least 15 nm. In the meanwhile, the standard deviation of the pore major diameter is preferably up to 100 nm, more preferably up to 70 nm, and still more preferably up to 50 nm in view of the structural strength of the membrane.

The degree of dispersion of the pore major diameter on the surface can be increased by stretching the large pores which inherently have high degree of pore diameter dispersion. When the pores on the surface are stretched, larger pores undergo larger deformation, and as a consequence, major diameter of the larger pores are increased to a larger degree upon increase in the degree of deformation while the major diameter of the smaller pores is not changed so much. This results in the increase of the major diameter dispersion. Exemplary methods used in increasing the dispersion of the pore diameter before the stretching include increase in the distribution of the weight average molecular weight of the hydrophilic polymer which is added to the spinning dope solution as a pore-forming agent to thereby facilitate inconsistent phase separation, and promotion of the phase separation to thereby promote such growth of surface pores. Since the pores grow by fusion with the adjacent pores in the progress of the phase separation, the pore growth depends on the probability of collision and the pores formed are inconsistent in size. The phase separation can be facilitated by adjusting the composition of the spinning dope solution, composition of the coagulation bath, temperature of the phase separation, time until the solidification, and the like.

Addition of the hydrophilic polymer to the spinning dope solution is also effective for the control of the phase separation. When a hydrophilic polymer is added to the spinning dope solution, solidification time when the main component constituting the dope solution is brought in contact with the poor solvent is suppressed, and this enables sufficient stretching with the progress of the phase separation, and the dispersion of the pore minor diameter is thereby reduced.

Since excessively high weight average molecular weight of the hydrophilic polymer added results in the loss of the compatibility with the spinning dope solution, the weight average molecular weight of the hydrophilic polymer is preferably up to 1,500,000, and more preferably up to 1,200,000 although the weight average molecular weight is not particularly limited. In the meanwhile, addition of a hydrophilic polymer having a small weight average molecular weight to the spinning dope solution is associated with the risk of elution of the hydrophilic polymer from the membrane. Accordingly, the weight average molecular weight of the hydrophilic polymer is preferably at least 20,000, and more preferably at least 40,000.

The weight average molecular weight of the hydrophilic polymer in the porous membrane may be measured, for example, by dissolving the porous membrane in a solvent, extracting the hydrophilic polymer by using a solvent which is a good solvent for the hydrophilic polymer and a poor solvent for the polymer structurally constituting the porous membrane, and measuring the weight average molecular weight of the hydrophilic polymer in the extract by gel permeation chromatography or the like. The conditions used in the extraction may be adequately adjusted depending on the combination of the polymer structurally constituting the porous membrane and the hydrophilic polymer. A more accurate measurement of the weight average molecular weight is enabled when the extract ratio of the hydrophilic polymer is high.

With regard to the poor solvent for the polymer which is the main component constituting the spinning dope solution, addition of such poor solvent facilitates progress of the phase separation, and this results in the higher effect of stretching the pores. The polymer which is the main component constituting the spinning dope solution is the polymer used at the highest content (by weight) in the polymers constituting the spinning dope solution. Although the optimal range may differ by the composition of the spinning dope solution and the type of the poor solvent, when the poor solvent used is water, the water content in the spinning dope solution is preferably at least 0.5% by weight and more preferably at least 0.8% by weight. In the meanwhile, excessive content of the poor solvent in the spinning dope solution results in the solidification of the spinning dope solution, and therefore, the water content is preferably up to 3% by weight.

In the present invention, the major diameter and the minor diameter of the pores formed on the surface can be measured from the image obtained by observing the surface with a scanning electron microscope (SEM). The minor diameter is the largest diameter in the minor axis direction, and the major diameter is the largest diameter in the major axis direction. All pores in arbitrarily chosen area of 1 μm×1 μm recognizable by observation using SEM at a magnification of 50,000 are analyzed. When the total number of the pores measured is less than 50, the measurement in the area of 1 μm×1 μm is repeated until the total pore numbers reached at least 50 to add to the data. Arithmetic average and standard deviation are calculated from the measurement by rounding the number to the 1 decimal place. The standard deviation is the standard deviation (sample standard deviation) estimated on the samples calculated by the following equation:

$$\text{Standard deviation}=\{\Sigma(a-b)^2/(c-1)\}^{1/2}$$

wherein a is the average of the pore diameter, b is the pore diameter measured, and c is the number of the pore diameter measured.

With regard to the pores formed on the other surface (for example, the outer surface not affecting the fractionation performance when the porous membrane is a hollow fiber membrane and the fine pores are formed on the inner surface), average of the ratio of the pore major diameter to the pore minor diameter is preferably at least 1.5 in view of improving the water permeability. In the meanwhile, the average of this ratio is preferably up to 4, and more preferably up to 3 since excessively high average of the ratio may result in the brittle membrane structure, and hence, reduced strength. The average of the minor diameter of the pores formed on the outer surface is preferably at least 0.2 μm, and more preferably at least 0.3 μm in view of the performance such as water permeability and friction when made into fiber bundle. In the meanwhile, the average of the pore minor diameter is preferably up to 0.6 μm in view of the fiber strength.

The pore diameter of the outer surface can be adjusted by the conditions of the dry section after the ejection of the dope solution as will be described below.

The porous membrane will have an increased water permeability when the porous membrane surface has an increased porosity due to the increase in the water flow path. On the other hand, the surface will be provided with a higher structural strength by reducing the porosity. Accordingly, the porosity of the porous membrane surface is preferably at least 1%, and more preferably at least 3%. On the other hand, the porosity is preferably less than 10%, and more preferably up to 8%.

The porosity can be effectively increased by increasing the amount of the hydrophilic polymer added to the spinning dope solution.

The surface porosity may be measured by using an image taken in the observation of the porous membrane surface with the SEM. More specifically, any area of 1 μm×1 μm in the image of the surface at a magnitude of 50,000 is processed to binarize the membrane structural part and the pore part, and the area percentage of the pore area in the area measured is calculated for use as the porosity.

Structure of the porous membrane in the thickness direction is classified into a symmetrical membrane structure wherein the pore diameter is substantially constant and an asymmetrical membrane wherein the pore diameter continuously or incrementally change so that one of the surface, the membrane interior, and the other surface have different pore diameter. Of these, the layer with small pore diameter contributing for the size exclusion is thin in the case of the asymmetrical membrane, and such membrane exhibits low resistance for the water permeation, and hence, high water permeability. Accordingly, an asymmetrical structure is preferable for the structure of the membrane in the thickness direction. In this case, it is usual that only one surface of the membrane is the surface satisfying the (A) and (B).

More specifically, higher asymmetry is advantageous for the water permeability. Accordingly, in the preferable embodiment of the porous membrane used for hemodiafiltration, average of the minor diameter of the pores on the other surface is at least 0.1 μm, and more preferably at least 0.2 μm although the pore size is not particularly limited. In the meanwhile, the average of the minor diameter of the pores on such surface is preferably up to 0.6 μm, and more preferably up to 0.5 μm in view of the structural strength of the membrane. The term "the other surface" as used herein is the surface opposite to the surface where pores satisfying the (A) and (B) are formed. In other words, the membrane is asymmetrical, and one surface is formed with pores with minute pore diameter satisfying the (A) and (B) while the other surface is formed with pores having the pore diameter as defined above.

In addition, ratio of the major diameter to the minor diameter of the pores on such surface is preferably at least 1.5 and up to 3 in view of the structural strength of the membrane.

The material constituting the main component of the porous membrane is preferably an amorphous polymer. An amorphous polymer is a polymer which does not experience crystallization, and which shows no exothermic peak by the crystallization in the measurement by differential scanning calorimeter.

Amorphous polymers are susceptible to experience structural deformation, and this enables efficient stretching of the pores. Control of the structure in the membrane thickness direction is also facilitated. It has been known that a porous membrane made of the amorphous polymer is prepared by inducing phase separation of a spinning dope solution that has been prepared by dissolving the amorphous polymer in a solvent by using heat or poor solvent and removing the solvent component. Since the amorphous polymer in the solvent is highly mobile, the amorphous polymer aggregates during the phase separation, and this enables increase in the concentration and formation of a dense structure. By using different phase separation speed in the membrane thickness direction, a membrane having an asymmetrical structure wherein pore diameter is different in the membrane thickness direction can be prepared.

Examples of the amorphous polymer used for the material of the porous membrane include acryl polymers, vinyl acetate polymers, and polysulfone polymers. Of these, the preferred is used of a polysulfone polymer in view of easy control of the pore diameter. The term "polysulfone polymer" used in the present invention is a polymer having an aromatic ring, sulfonyl group, and ether group in the backbone. Exemplary non-limiting preferable polysulfone polymers include those represented by the following chemical formulae (1) and (2). In the formula, n is, for example, an integer of 50 to 80.

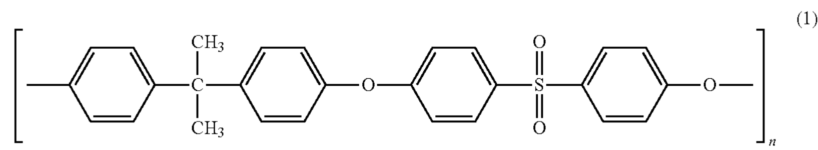

(1)

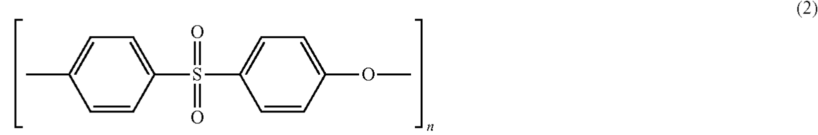

(2)

Examples of the polysulfone include Udel (Registered Trademark) polysulfone P-1700 and P-3500 (manufactured by Solvay), Ultrason (Registered Trademark) S3010 and S6010 (manufactured by BASF), VICTREX (Registered Trademark) (manufactured by Sumitomo Chemical Co., Ltd.), and Radel (Registered Trademark) A (manufactured by Solvay). Although the polysulfone used in the present invention is preferably a polymer solely comprising the constitutional repeating unit represented by the formula (1) and/or (2), the polysulfone may be in the form of a copolymer with other monomer to the extent not adversely affecting the merits of the invention. Content of such other monomer is preferably up to 10% by weight although such content is not particularly limited.

When a hydrophilic polymer is added to the spinning dope solution, the resulting porous membrane will contain the hydrophilic polymer, and the thus improved water wettability results in the improved water permeability. In addition, the effect of stretching the pores will be insufficient even if the draft ratio or the ratio of the cross-sectional area of the slit to the cross-sectional area of the membrane is increased as described above if the dope solution contains no hydrophilic polymer. Furthermore, provision of the hydrophilicity also has the effect of improving the biocompatibility. Accordingly, the porous membrane preferably contains at least 0.5% by weight, and more preferably at least 1% by weight of the hydrophilic polymer. On the other hand, excessively high content of the hydrophilic polymer in the porous membrane results in the increase of the eluate, and the hydrophilic polymer is preferably up to 8% by weight, more preferably up to 6% by weight, and still more preferably up to 4% by weight.

The method used for measuring the content of the hydrophilic polymer should be determined by considering the polymer type. Typical method is elementary analysis.

When the surface of the porous membrane should be provided with hydrophilicity, a selective provision may be accomplished by means of adding a hydrophilic polymer to the coagulation solution or by conducing the coating of the surface after the membrane production. In particular, in the case of a hollow fiber membrane, if a hydrophilic polymer is added to the injection liquid used in the ejection, the spinning dope solution will be in contact with the injection liquid to cause phase separation, and the hydrophilic polymer will be diffused to the side of the dope solution in the course of coagulation to facilitate incorporation of the hydrophilic polymer. When the polymer mainly constituting the porous membrane is a hydrophobic polymer, incorporation efficiency into the membrane surface can be improved by using a hydrophilic polymer containing a hydrophobic unit, namely, by utilizing the interaction between the hydrophobic moieties.

Exemplary non-limited examples of the hydrophilic polymer include polyethylene glycol, polyvinylpyrrolidone, polyethyleneimine, polyvinyl alcohol, derivatives thereof, and polymerization product of such hydrophilic polymer with other monomer.

The hydrophilic polymer may be adequately selected by considering affinity with the material used for the porous membrane or the solvent. In the case of a polysulfone polymer, the preferred is use of polyvinylpyrrolidone in view of the high compatibility although not particularly limited.

In the case of a porous membrane used for blood purification purpose, amount of the hydrophilic polymer on the surface that is brought in contact with the blood, namely, the surface provided with the pores satisfying the (A) and (B) of the present invention (preferably the inner surface in the case of a hollow fiber membrane) is important. Insufficient amount of the hydrophilic polymer on such surface will lead to an insufficient blood compatibility, and hence, an increased risk of blood coagulation. Accordingly, the amount of the hydrophilic polymer on the surface that is brought in contact with the blood is preferably at least 20% by weight, more preferably at least 22% by weight, and still more preferably at least 25% by weight. In the meanwhile, excessive hydrophilic polymer will lead to an increase in the amount of the hydrophilic polymer eluting into the blood, and the thus eluted polymer may cause side effects and complications. Accordingly, the amount of the hydrophilic polymer on the surface is preferably up to 45% by weight, and more preferably up to 42% by weight.

The hydrophilic polymer on the porous membrane surface can be measured by means of X-ray photoelectron spectroscopy (XPS). The value used is the one measured at a take-off angle of 90°. At the take-off angle of 90°, an area from the surface to the depth of about 10 nm are detected. The value used is the average of measurements at 3 different sites. For example, when the hydrophobic polymer is a polysulfone and the hydrophilic polymer is a polyvinylpyrrolidone, content of the polyvinylpyrrolidone on the surface is calculated from the measurements of nitrogen content (d (atom %)) and the sulfur content (e (atom %)) by the following equation:

$$\text{Polyvinylpyrrolidone content } (f)=100\times(d\times 111)/(d\times 111+e\times 442)$$

In view of preparing a spinning dope solution, solubility at a high temperature is important for improving the solubility in use. However, dissolution at a high temperature is associated with the risk of change in the composition by thermal denaturing of the polymer and evaporation of the solvent. Accordingly, the solution temperature is preferably at least 30° C. and up to 120° C. while the optimal solution temperature may vary by the types of the polymer and the additives used.

Adequate form of the porous membrane may be selected from flat membrane, tubular membrane, hollow fiber membrane, and the like depending on the application. Although not particularly limited, the porous membrane is preferably a hollow fiber membrane in view of the large membrane area per unit volume, namely, capability of compact accommodation of the membrane having the large area. A hollow fiber membrane is produced by ejecting an injection liquid or an injection gas from the cylindrical tube in the interior the double tube spinneret and ejecting the spinning dope solution from the slit on the outer side. The structure of the inner surface of the hollow fiber membrane can be controlled by adjusting the concentration and temperature of the poor solvent of the injection liquid, or by adding the additive. Accordingly, the minor diameter of the pores should be controlled on the inner surface of the hollow fiber membrane.

The porous membrane of the present invention is the one produced by the production method comprising the steps of ejecting a spinning dope solution from a the slit formed in a spinneret and the step of solidifying the spinning dope solution in a coagulation bath after allowing the spinning dope solution pass through a gas phase dry section, although the production method is not particularly limited. When the phase separation is induced by heat, the spinning dope solution is solidified by quenching in the coagulation bath after cooling in the dry section. When the phase separation is induced by the poor solvent, the spinning dope solution is ejected so that the spinning dope solution is in contact with a coagulating solution containing the poor solvent for the main component of the spinning dope solution, and the spinning dope solution is further solidified in a coagulation bath comprising the poor solvent for the main component. In the method wherein the phase separation is induced by the poor solvent, the poor solvent is supplied in the direction of the membrane thickness by diffusion and difference in concentration of the poor solvent is caused in the direction of the membrane thickness to facilitate formation of the asymmetric structure.

Accordingly, the coagulation solution containing the poor solvent and the spinning dope solution are preferably brought in contact with each other in the dry section.

When the concentration of the coagulation solution is adjusted as a mixture of a poor solvent and a good solvent, coagulability will be changed, and the pore diameter on the surface will be changed.

A poor solvent is a solvent to which the main component polymer constituting the spinning dope solution is not soluble at the membrane formation temperature. Although not particularly limited, use of water for the solvent wherein the polysulfone polymer is hardly soluble is preferable for the poor solvent. Preferable non-limiting examples of the good solvent include N,N-dimethylacetamide.

Preferable range of the composition of the coagulation solution varies with the conditions such as the composition of the spinning dope solution, type of the poor solvent and the good solvent, and the like. When the concentration of the good solvent is too low, the coagulation proceeds at a higher speed, and the pore diameter will be small and the effect of the stretching will be insignificant. Accordingly, concentration of the good solvent of the coagulation solution is preferably at least 40% by weight and more preferably 50% by weight. In the meanwhile, excessively high concentration of the good solvent adversely affects the coagulation of the spinning dope solution and this may result in the poor spinnability. Accordingly, the concentration of the good solvent is preferably up to 80% by weight and more preferably up to 70% by weight.

As described above, the major diameter of the pores on the surface can be increased in relation to the minor diameter by increasing in the draft ratio and conducting the stretching before the solidification. Since the stretching is conducted before the solidification of the dope solution, breakage and cracking inherent to the stretching does not occur. The draft ratio is typically at least 1.5, preferably at least 2, and more preferably at least 2.5. On the other hand, excessively high draft ratio results in the yarn breaking, and therefore, the draft ratio should be up to 10, and preferably up to 9.

When the dope solution has a high viscosity, stress in the stretching will be increased, and the effect of elongating the surface pores will be improved, and the major diameter will be increased in relation to the minor diameter. Since the viscosity increases with the progress of the phase separation, stretching under the high viscosity conditions is enabled by extending the time of passing through the dry section to thereby extend the time allowed for the progress of the phase separation. The time of the passage through the dry section is preferably at least 0.3 seconds, and more preferably at least 0.5 seconds although the passage time may depend on the conditions affecting the progress of the phase separation such as composition and temperature of the spinning dope solution. In the meanwhile, the passage time is preferably up to 1.5 seconds and more preferably up to 1 second. Furthermore, in the case of a hollow fiber, phase separation on the outer surface side can be induced by contacting with wet air in the dry section, and accordingly, humidity of the wet air is preferably at least 50%, more preferably at least 60%, and still more preferably at least 70%. Since progress of the phase separation is likely to be insufficient at low wet air temperature, the temperature of the wet air is preferably at least 10° C., and more preferably at least 20° C. In the meanwhile, the temperature of the wet air is preferably up to 60° C., and more preferably up to 40° C. since excessively high temperature may invite loss of spinnability.

The viscosity of the spinning dope solution can be increased by increasing the amount of the polymer constituting the main component of the spinning dope solution and/or the hydrophilic polymer, by adding a thickener, or by using a lower ejection temperature. However, when the viscosity of the spinning dope solution is too low, the stress in the stretching will be low, and this adversely affects the effect of elongating the pores, and therefore, the viscosity of the spinning dope solution at the ejection temperature is preferably at least 0.5 Pa-s, and more preferably at least 1.0 Pa·s. In the meanwhile, an excessively high viscosity of the spinning dope solution invites increase in the ejection pressure, and hence, instability in the spinning, and therefore, the viscosity is preferably up to 20 Pa·s and more preferably up to 15 Pa·s.

When a large amount of hydrophilic polymer is added to the spinning dope solution, amount of the hydrophilic polymer at the boundary between the pores and the structure increases in the formation of the pores of the porous membrane, and this results in the more tangling of the polymer molecular chain in the structure to suppress the deformation of the pores. On the other hand, increase in the amount of the hydrophilic polymer results in the increase of the pore number, and hence, increase in the porosity of the surface of the porous membrane. Accordingly, concentration of the hydrophilic polymer in the spinning dope solution is preferably up to 70% by weight, and more preferably up to 60% by weight of the concentration of the polymer which is the main component of the porous membrane. In the meanwhile, since the porosity of the surface can be increased by increasing the concentration of the hydrophilic polymer, the concentration of the hydrophilic polymer is preferably at least 10% by weight, and more preferably at least 20% by weight of the concentration of the polymer which is the main component of the spinning dope solution.

The spinneret temperature during the ejection affects the viscosity and phase separation behavior of the spinning dope solution. Generally, use of higher spinneret temperature results in the higher water permeation of the resulting porous membrane as well as higher cut-off molecular weight. An excessively high temperature, however, invites decrease in the viscosity and coagulability of the spinning dope solution, and hence, unstable ejection and poor spinnability. In the meanwhile, an excessively low spinneret temperature may result in dew condensation, and hence, moisture deposition on the double tube spinneret. Accordingly, the spinneret temperature is preferably at least 20° C. and preferably up to 90° C. on the other hand.

After the ejection of the spinning dope solution from the spinneret, the ejected dope is preferably passed through the coagulation bath to fix the membrane structure. The temperature of the coagulation bath is preferably in the range of 20 to 90° C. The preferable composition is 60 to 100% of water and 40 to 0% of the good solvent used for the spinning dope solution.

The membrane after passing the coagulation bath is preferably passed through a water washing bath to remove the remaining solvent and the like. The water washing bath is preferably adjusted to a temperature range of 60 to 90° C. since washing can be done at an increased efficiency when the temperature is higher.

The thus produced porous membrane may be dried. Exemplary methods used for the drying include drying by hot air, drying by microwave, and drying under reduced pressure, and the preferred is the hot air drying.

In addition, when the porous membrane is a hollow fiber membrane, crimping is useful since the flow of the dialysis solution in the resulting module is improved. The membrane is preferably crimped at a pitch in the range of 5 to 30 mm and an amplitude in the range of 0.2 to 3 mm.

The thickness of the porous membrane may be adequately determined in view of the pressure applied in the use and diffusion performance. The thickness is preferably at least 20 μm and more preferably at least 25 μm since an excessively thin membrane may not endure the pressure applied in the use. On the other hand, excessively thick membrane may invite increase in the water permeation resistance, and hence, reduced water permeability, and therefore, the thickness is preferably up to 50 μm and more preferably up to 45 μm.

When the porous membrane is a hollow fiber membrane, pressure resistance is correlated with the ratio of the membrane thickness to the inner diameter, and a high ratio of the membrane thickness to the inner diameter may invite increase in the pressure resistance. When the inner diameter is reduced, the module size can be reduced and the pressure resistance will be improved. However, a membrane with reduced inner diameter is produced by reducing the diameter in the production of the membrane, and a star-shaped fiber with wrinkled interior is likely to be produced. Phase separation is inconsistent in such star-shaped fiber and this invites increased the pore diameter dispersion, and the fractionation performance is thereby reduced. Accordingly, inner diameter of the hollow fiber membrane is preferably at least 80 μm, more preferably at least 100 μm, and still more preferably at least 120 μm, and also, preferably up to 250 μm, more preferably up to 200 μm, and still more preferably up to 160 μm.

The inner diameter of the hollow fiber membrane is the value obtained by measuring each of the membrane thickness of 16 randomly selected hollow fiber membranes with a lens of 1,000 magnifications of Microwatcher (VH-Z100 manufactured by KEYENCE) and calculating the average a, and conducting the calculation by the following equation. The outer diameter of the hollow fiber membrane is determined by measuring the outer diameter of each of 16 randomly selected hollow fiber membranes with a laser displacement gage (for example, LS5040T manufactured by KEYENCE) and calculating the average.

Inner diameter of the hollow fiber membrane (μm)=outer diameter of the hollow fiber membrane−2×membrane thickness The water permeation of the porous membrane is preferably at least 200 mL/hr/m$^2$/mmHg, more preferably at least 500 mL/hr/m$^2$/mmHg, and still more preferably at least 800 mL/hr/m$^2$/mmHg. However, the water permeation of the porous membrane is preferably up to 2500 mL/hr/m$^2$/mmHg, more preferably up to 2200 mL/hr/m$^2$/mmHg, and still more preferably up to 2000 mL/hr/m$^2$/mmHg since excessively high water permeation invites increase in the inner filtration and this results in the increased solute removal performance while stimulation to the blood corpuscle will also be increased in the case of the blood purification application. The water permeability (UFR) is calculated by the following equation:

$$UFR\ (\text{mL/hr/m}^2\text{/mmHg})=Qw/(P\times T\times A)$$

wherein Qw is filtrate volume (mL), T is time of filtration (hr), P is pressure (mmHg), and A is surface area of the interior of the hollow fiber membrane (m$^2$).

An index of the fractionation performance used for hollow fiber membrane is dextran sieving coefficient. Dextran sieving coefficient is the proportion of the dextran permeating through the membrane when the dextran aqueous solution is filtered through the hollow fiber membrane, and this value is determined for each weight average molecular weight. The dextran sieving coefficient is calculated by the following equation:

$$\text{SC}=2Cf/(Ci+Co)$$

wherein SC is the dextran sieving coefficient, Ci is the concentration of the aqueous solution supplied to the separation membrane, Co is the concentration of the aqueous solution remaining on the supply side after the filtration, and Cf is the concentration of the filtrate. The dextran concentration for each molecular weight may be measured by a method such as gel permeation chromatography. In the measurement, calibration curves of the molecular weight and the concentration may be depicted by using dextran solutions having known molecular weight and concentration. The hollow fiber membrane can be determined to have a higher separation performance when absolute value of the slope of the fractionation curve depicted by plotting the values of the dextran sieving coefficient for each molecular weight is high, and in particular, when the absolute value of the slope of the fractionation curve in the range of the sieving coefficient of 0.45 to 0.55 is high. The absolute value of the slope of the fractionation curve is the value obtained by rounding the number to the second decimal place. The absolute value of the slope of the fractionation curve is preferably at least 1.35, more preferably at least 1.40, and still more preferably at least 1.45. The molecular weight when the dextran sieving coefficient is 0.1 is used for the cut-off molecular weight.

Although the method used for accommodating the porous membrane of the present invention in the module is not particularly limited, an exemplary accommodation when the porous membrane is a hollow fiber membrane may be accomplished by cutting the hollow fiber membrane to the required length; preparing bundles of necessary number of membranes; placing the bundle in a cylindrical case; placing tentative caps at opposite ends of the cylindrical case; pouring a potting agent at opposite ends of the hollow fiber membrane (preferably by introducing the potting agent while rotating the module by a centrifuge so that the potting agent can be evenly filled); cutting opposite ends so that opposite ends of the hollow fiber membrane are left open after the solidification of the potting agent; mounting headers at opposite ends of the case; and plugging the header and the spinneret section of the case to obtain the hollow fiber membrane module. In view of facilitating even flow of the dialysis solution, the hollow fiber membrane module is preferably filled to the range of 30 to 70%, and more preferably 40 to 60%.

For the purpose of biocompatibility and suppressing the fouling with the protein, the surface of the porous membrane may be provided with a polymer or the like to the extent not adversely affecting the membrane performance. Exemplary method used for improving the biocompatibility of the hollow fiber membrane by covering the membrane surface with the polymer include addition of the polymer to the spinning dope solution of the hollow fiber membrane, addition of the polymer to the injection liquid used in producing the hollow fiber membrane, and coating of the polymer on the membrane surface after producing the hollow fiber membrane. Preferable non-limited solution used for the coating is an aqueous solution. The "membrane surface" as used herein means the surface that is brought in contact with the liquid to be treated such as blood in the case of a dialysis membrane.

More specifically, when the coating is conducted in the case wherein the porous membrane is a hydrophobic polymer and the polymer used for the coating is a hydrophilic polymer, consistent coating of the porous membrane surface is enabled when adsorption equilibrium constant of the hydrophobic polymer and the hydrophilic polymer in the coating solution is high. Accordingly, the hydrophilic polymer used for the coating preferably contains a hydrophobic group.

In addition, the polymer used is preferably an ester group-containing polymer since presence of an ester group on the membrane surface prevents deposition of proteins and platelets although particular mechanism is unknown. In view of the above, exemplary non-limiting polymers used for the coating include vinyl carboxylates such as vinyl acetate, acrylates such as methyl acrylate and methoxyethyl acrylate, methacrylates such as methyl methacrylate, ethyl methacrylate, and hydroxyethyl methacrylate, polyvinyl alcohol having a degree of saponification of less than 99%, vinyl pyrrolidone-vinyl acetate copolymer, vinyl pyrrolidone-vinyl caprolactam copolymer, and vinyl pyrrolidone-vinyl alcohol copolymer. Of these, the preferred is vinyl pyrrolidone-vinyl acetate copolymer.

For example, when the ester group-containing polymer used is Kollidon VA64 (BASF) which is a copolymer (6/4) of vinyl pyrrolidone and vinyl acetate, preferable range for the amount of the VA64 in the spinning dope solution is 1 to 10% by weight, spinneret temperature is 20 to 60° C., temperature of the dry section is 10 to 60° C., and relative humidity is 70 to 95% RH. When an ester group-containing polymer is added to the injection liquid, the compositional ratio of the injection liquid, temperature of the injection liquid, composition of the spinning dope solution, and the like may have the effects. In the case of VA64, the amount added to the injection liquid is preferably 0.001 to 10% by weight, the temperature of the injection liquid is preferably 10 to 60° C., and the composition of the spinning dope solution is preferably such that the concentration of the polysulfone polymer concentration is 14 to 25% by weight. In the case of polyvinylpyrrolidone, the preferred is 2 to 10% by weight. In order to suppress the diffusion of the VA64 in the membrane, the polysulfone polymer preferably has a smaller weight average molecular weight, and use of the one having a molecular weight of up to 100,000, and in particular, up to 50,000 is preferable. When the polysulfone polymer is subjected to a post-treatment such as coating, concentration of the ester group-containing polymer in the coating solution, contact time, temperature in the coating may have the effects. For example, when VA64 aqueous solution is used for the coating, the VA64 concentration is preferably 1 to 5000 ppm, the contact time is preferably at least 10 seconds, and the temperature is 10 to 80° C. In the case when the coating is conducted continuously and not in batchwise, the coating will have a higher evenness when the flow rate of the VA64 aqueous solution is higher. However, coating of sufficient amount cannot be accomplished when the flow rate is too high, and therefore, the preferable range is 200 to 1000 mL/min. Furthermore, the polymer coated on the membrane surface is immobilized by means of radiation, heat treatment, chemical reaction, or the like.

Amount of the ester groups on the membrane surface may be measured by electron spectroscopy for chemical analysis (hereinafter also referred to as ESCA), and area percentage of the carbon peak corresponding to the ester group is typically at least 0.1 (atom %), preferably at least 0.5 (atom %), and more preferably at least 1 (atom %). In the meanwhile, since excessive amount of the ester group may result in the loss of the membrane performance, the area percentage is preferably up to 10 (atom %), and preferably up to 5 (atom %).

In the measurement by ESCA, the measurement used is the one measured at the take-off angle of 90°. At the take-off angle of 90°, an area from the surface to the depth of about 10 nm are detected. The value used is the average of measurements at 3 different sites. The carbon peak corresponding to the ester group (COO) is obtained by peak splitting of the peak at +4.0 to 4.2 eV from the main peak of CH and C—C of C1s. The amount of the carbon (atom %) corresponding to the ester group may be determined by calculating the proportion of the particular peak area in relation to all elements. More specifically, Cis is constituted from 5 components, namely, the component mainly corresponding to $CH_x$, C—C, C═C, and C—S, the component mainly corresponding to C—O and C—N, the component corresponding to π-π*satellite, the component corresponding to C═O, and the component corresponding to COO. Accordingly, the peak is split into 5 components. The component corresponding to COO is the peak at +4.0 to 4.2 eV from the main peak of $CH_x$ and C—C (near 285 eV). Peak area ratio of these components is calculated by rounding the number to the 1 decimal place. The calculation may be conducted by multiplying the carbon amount (atom %) of the Cis by the peak area ratio of the component corresponding to COO. When the result of the peak splitting is up to 0.4%, the result is evaluated below the detection limit.

In the case of the dialysis membrane used for hemodiafiltration, protein may deposit on the surface of the membrane to cause fouling due to the filtration of the large amount of the liquid, and this may cause the problem of reduced removal performance and increase of the transmembrane pressure (TMP). As described above, the porous membrane having the ester group on the surface that becomes in contact with the liquid to be treated is capable of suppressing the protein fouling, and such membrane is preferable since decrease in the removal performance and increase in the TMP can be suppressed.

Change over time of the albumin sieving coefficient (Sc-Alb) during use of the hollow fiber membrane was measured as an index of the stability of the membrane performance over time. Albumin is one of proteins which are useful for human body, and in recent hollow fiber membrane modules, with the increase in the pore diameter of the membrane to facilitate removal of the uremia protein (also referred to as the low molecular weight protein), there is a demand for the fractionation performance capable of suppressing excessive permeation or loss of the albumin while allowing permeation of the low molecular weight protein having smaller molecular weight, and therefore, the albumin sieving coefficient has become a typical index for the separation performance of the membrane. In other words, the stability of the hollow fiber membrane module performance over time can be found out by measuring the change over time of the albumin sieving coefficient.

Change over time of the sieving coefficient of albumin was measured by the procedure as described below. Bovine blood having sodium citrate added thereto was adjusted so that hematocrit was 30%, total protein concentration was 6.5 g/dl, 37° C., and 2 L. The dialyzer used was TR2000S manufactured by Toray Medical Co., Ltd.

Water removal rate of the dialyzer was set at 10 ml/(min×m$^2$). Bi circuit inlet section was placed in a circulation beaker filled with 2 L of the bovine blood (37° C.) which has been prepared as described above, and Bi pump was started (flow rate, 200 mL/min). Immediately after discarding the fluid discharged from Bo circuit outlet section for 90 seconds, the Bo circuit outlet section and Do circuit outlet section were placed in the circulation beaker to start the circulation phase.

Next, water removal pump of the dialyzer is started, and sampling is conducted at a regular interval from each of the Bi, Bo, and Do. Albumin concentration with lapse of time is measured, and the albumin sieving coefficient at each sampling is calculated by the following equation:

$$\text{Sc-Alb}\ (\%)=CDo/(CBi+CBo)$$

wherein CDo is albumin concentration (g/ml) at the Do circuit outlet section, CBo is albumin concentration (g/ml) at the Bo circuit outlet section, and CBi is albumin concentration (g/ml) at the Bi circuit inlet section.

Fouling prevention performance is higher when the ratio of the value B at 60 to 240 minutes after the blood introduction to the value A at 5 to 10 minutes after the blood introduction (B/A) is higher, and the ratio B/A is preferably at least 0.4, more preferably at least 0.5, and more preferably at least 0.6.

When this procedure is conducted under pre-dilution conditions of the hemodiafiltration, the bovine blood prepared by adding 1.8 L of physiological saline to 2.2 L of the bovine blood having a hematocrit of 30% and a total protein concentration of 6.0 g/dl is used, and the procedure as described above is repeated at a blood flow rate of 450 mL/mi and a water removal rate of 200 mL/min.

The porous membrane used in the blood purification application such as artificial kidney should be sterilized, and the sterilization is mostly conducted by the use of radiation in view of low residual toxicity and convenience. Exemplary radiations include α ray, β ray, γ ray, X ray, UV radiation and electron beam. The preferable radiations used are γ ray and electron beam in view of low residual toxicity and convenience. In addition, the irradiation with the radiation beam is also preferable since the hydrophilic polymer incorporated in the porous membrane is immobilized by crosslinking with the membrane material caused by the radiation irradiation and this leads to decrease of the eluate. The sterilization effect will be insufficient when the radiation dose of the radiation is low while use of excessive radiation dose invites decomposition of the hydrophilic group-containing polymer and the membrane material, and hence, loss of biocompatibility. Accordingly, the radiation dose is preferably at least 15 kGy and up to 100 kGy.

EXAMPLES

(1) Measurement of Water Permeability

An exemplary measurement is described for the case wherein the porous membrane is a hollow fiber membrane.

40 hollow fiber membranes were filled in a housing having a diameter of about 5 mm and a length of 17 cm, and opposite ends of the housing were potted with epoxy resin chemical reaction-type adhesive "Quick Mender" (Registered Trademark) manufactured by Konishi Co., Ltd. and forming an opening by cutting to prepare the hollow fiber membrane module. Next, the hollow fiber membrane in the module and the interior of the module were washed for 30 minutes with distilled water. The filtrate volume per unit time was measured by applying a water pressure of 100 mmHg to the interior of the hollow fiber membrane and measuring the amount of water flowing out of the hollow fiber membrane. The water permeability (UFR) was calculated by the following equation:

$$UFR\ (\text{mL/hr/mmHg/m}^2)=Qw/(P\times T\times A)$$

wherein Qw is filtrate volume (mL), T is time of filtration (hr), P is pressure (mmHg), and A is surface area of the interior of the hollow fiber membrane (m$^2$).

(2) Method of Measuring the Sieving Coefficient of the Dextran

The measurement is described for the case wherein the porous membrane is a hollow fiber membrane.

The hollow fiber membrane module used in the measurement of (1) was used. Aqueous solutions of dextran (dope solution) were prepared by dissolving dextran having an average molecular weight of up to 1500 (No. 31394), an average molecular weight up to 6000 (No. 31388), an average molecular weight of 15000 to 20000 (No. 31387), an average molecular weight up to 40000 (No. 31389), an average molecular weight up to 60000 (No. 31397), and an average molecular weight up to 200000 (No. 31398) manufactured by FULKA in distilled water so that each solution was 0.5 m/mL (total solute, 3.0 mg/mL). The dope solution was applied to the module so that the solution would flow through the interior of the hollow fiber membrane for filtration to the exterior of the hollow fiber membrane. The dope solution was used at a temperature of 37° C., and the flow rate was adjusted so that the dope solution flow rate was 15 mL/min and the filtrate flow rate was 0.36 mL/min. At 15 minutes to 23 minutes after the passage of the dope solution, the solution at the inlet, the solution at the exit, and the filtrate were collected to measure the concentration by GPC. The GPC was conducted by filtering the sampled aqueous solution with a filter having the minute pore diameter of 0.45 μm, and applying the filtrate to a GPC column (TSK-gel-G3000PWXL manufactured by Tosoh Corporation) at a column temperature of 40° C. with the distilled water for liquid chromatography as the mobile phase, at a flow rate of 1 mL/min and a sample charge amount of 100 μL and using a differential refractometer (RI-8020 manufactured by Tosoh Corporation) at a sampling rate of 0.01 min and a base-line-range of 4.5 to 11.0 min. Calibration curves of the weight average molecular weight of the dextran were depicted immediately before the measurement by using monodispersed dextran (dextran standard No. 31416, No. 31417, No. 31418, No. 31420, and No. 31422 manufactured by FULKA). The sieving coefficient (SC) at each weight average molecular weight was calculated from dextran concentration of the solution at the dope solution inlet of the module (Ci), dextran concentration (Co) of the solution at the outlet, and dextran concentration of the filtrate (Cf) according to the following equation:

$$\text{SC}=2Cf/(Ci+Co)$$

As an index of separation performance, absolute value of the slope of the fractionation curve (s) was calculated by the following equation from the weight average molecular weight when SC is 0.45 ($MW_{0.45}$) and the weight average molecular weight when SC is 0.55 ($MW_{0.55}$). Higher absolute value of the s corresponds to the higher separation performance. The value s used was the value obtained by rounding the number to the two decimal place.

$$s=(0.45-0.55)/(\log MW_{0.45}-\log MW_{0.55})$$

The weight average molecular weight when SC is 0.1 was used for the cut-off molecular weight.

(3) Analysis of Minute Nitrogen

The procedure is described for the case wherein the amorphous polymer constituting the porous membrane is polysulfone and the hydrophilic polymer is polyvinylpyrrolidone.

The sample used for the analysis was prepared by freezing the porous membrane, pulverizing the frozen membrane, and drying the membrane for 2 hours at normal temperature under reduced pressure. The apparatus and conditions used for the measurement are:

Measurement apparatus: nitrogen micro-detector ND-100 (manufactured by Mitsubishi Chemical)
Electric furnace temperature (horizontal reactor)
thermal decomposition section: 800° C.
catalyst section: 900° C.
Main $O_2$ flow rate: 300 mL/min
$O_2$ flow rate: 300 mL/min
Ar flow rate: 400 mL/min
Sens: Low The measurement was conducted 3 times and the average was used for the measurement (N). The value was corrected to 2 significant figures.

Since polysulfone does not contain nitrogen atom, the nitrogen detected is solely from polyvinylpyrrolidone. Accordingly, amount of the polyvinylpyrrolidone in the porous membrane can be calculated by the following equation:

$$\text{Amount of polyvinylpyrrolidone (\% by weight)}=100\times(N\times 111)/14$$

(4) Measurement of Surface Pore Diameter

The measurement is described for the case wherein the porous membrane is a hollow fiber membrane and the inner surface is the dense layer.

The hollow fiber membrane was cut in half in axial direction to expose the interior surface. The inner surface of the hollow fiber membrane was observed by scanning electron microscope (SEM) (S-5500 manufactured by Hitachi High-Technologies Corporation) at a magnitude of 50,000 to take the image into the computer.

The largest diameter in the minor axis direction was used for the "minor diameter of the pore", and the largest diameter in the major axis direction was used for the "major diameter". All pores in an arbitrarily chosen area of 1 μm×1 μm were analyzed by using an image processing software (ImageJ developed by NIH). The SEM image was binarized to obtain an image wherein the hollow part is black and the structural part is white. When the hollow part and the structural part could not be clearly binarized due to the insufficient contrast of the analyte image, the image was processed after coloring the hollow part in black, and average and standard deviation were calculated from the minor and major diameters of the area analyzed. In this process, the pores having an area of up to 0.0001 $\mu m^2$ were excluded to cut the noise. In addition, ratio of the major diameter to the minor diameter was determined for each pore, and average of this ratio was also calculated. When the porous membrane is a hollow fiber membrane and the outer surface is dense, the same measurement may be carried out for the outer surface. In the case of a flat membrane, the same measurement may be carried out for the surface having the smaller pores. However, the type and the magnitude of the microscope may be adequately changed by the size of the pores.

(5) Measurement of Surface Porosity

The surface of the porous membrane was observed by repeating the procedure of (4), and the binarization was conducted for all pores in the selected area of 1 μm×1 μm in the resulting SEM image for analysis. Total area of the hollow parts was determined to calculate percentage of the total hollow area in the area analyzed to obtain the porosity. The same measurement was conducted for 3 locations, and the average was calculated.

(6) Measurement of Pore Diameter on the Opposite Surface

The measurement is described for the case wherein the porous membrane is a hollow fiber membrane and the inner surface is the dense layer.

The outer surface of the hollow fiber membrane was observed with an SEM (S-800 field-emission scanning electron microscope FE-SEM manufactured by Hitachi) at a magnitude of 3,000 to take the image into the computer. All pores in an arbitrarily chosen area of 20 μm×20 μm in the SEM image were analyzed by an image processing software (ImageJ developed by NIH). The SEM image was binarized to obtain an image wherein the hollow part is black and the structural part is white. When the hollow part and the structural part could not be clearly binarized due to the insufficient contrast of the analyte image, the image is processed after coloring the hollow part in black, and the average was calculated from the minor and major pore diameters of the area analyzed. When the porous membrane is a hollow fiber membrane and the outer surface was dense, the same measurement is carried out for the inner surface. In the case of a flat membrane, the same measurement is carried out for the surface with the larger pore diameter. However, the type and the magnitude of the microscope may be adequately changed by the size of the pores.

Example 1

16% by weight of polysulfone ("Udel" (Registered Trademark) P-3500 manufactured by Solvay), 4% by weight of polyvinylpyrrolidone (K30 manufactured by International Specialty Products hereinafter abbreviated by ISP), and 2% by weight of polyvinylpyrrolidone (K90 manufactured by ISP) were added to a mixed solvent of 77% by weight of N,N-dimethylacetamide and 1% by weight of water, and the mixture was heated to 90° C. for 6 hours for melting to thereby prepare a spinning dope solution. This spinning dope solution was ejected from annular slit of a double annulation spinneret. The annular slit had an outer diameter of 0.5 mm and an inner diameter of 0.25 mm. A solution comprising 63% by weight of N,N-dimethylacetamide and 37% by weight of water was ejected as an injection liquid from the inner tube. The spinneret was maintained at a temperature of 50° C. The ejected spinning dope solution was allowed to pass through the dry section (350 mm) having a dew point of 26° C. (temperature, 30° C.; humidity, 80%) in 0.7 second, guided to a water bath (coagulation bath) at 40° C. for solidification, taken up by the first roller outside the coagulation bath at a speed of 30 m/min, washed in a water bath at 60° C., and wound up by a reel. By adjusting ejection rate of the dope solution and the injection liquid, a porous membrane in the form of a hollow fiber membrane having a diameter (inner diameter) of 198 μm and a membrane thickness of 40.5 μm was obtained. The draft ratio was 2.7, and the ratio of the cross-sectional area of the slit to the cross-sectional area of the hollow fiber membrane was 4.9.

The measurement of the water permeability, the measurement of the dextran sieving coefficient, the measurement of the surface pore diameter, and the elementary analysis were conducted. The results are shown in Table 1. Picture of the surface of the porous membrane produced by the method of this Example was taken by a scanning electron microscope (SEM), and the picture is shown in FIG. 1.

A porous membrane having an asymmetrical structure was obtained. The minor diameter of the pores on the surface had a low average and a low standard deviation. The major diameter of the pores was sufficiently larger than the minor diameter of the pores. This porous membrane exhibited a high water permeability as well as high fractionation performance.

Example 2

The experiment was conducted by repeating the procedure of Example 1 except that the annular slit of the spinneret had an outer diameter of 0.73 mm and an inner diameter of 0.23 mm. The resulting porous membrane in the form of a hollow fiber membrane had a diameter (inner diameter) of 198 μm and a membrane thickness of 39 μm. The draft ratio was 7.6, and the ratio of the cross-sectional area of the slit to the cross-sectional area of the hollow fiber membrane was 13.0.

The measurement of the water permeability, the measurement of the dextran sieving coefficient, the measurement of the surface pore diameter, and the elementary analysis were conducted. The results are shown in Table 1.

As in the case of Example 1, the resulting porous membrane had a low average and a low standard deviation of the minor diameter, and the porous membrane exhibited a high water permeability as well as high fractionation performance.

Example 3

The experiment was conducted by repeating the procedure of Example 2 except that a solution comprising 60% by weight of N,N-dimethylacetamide and 40% by weight of water was used for the injection liquid. The resulting porous membrane in the form of a hollow fiber membrane had an inner diameter of 203 μm and a membrane thickness of 40 μm. The draft ratio was 7.6, and the ratio of the cross-sectional area of the slit to the cross-sectional area of the hollow fiber membrane was 12.5.

The measurement of the water permeability, the measurement of the dextran sieving coefficient, the measurement of the surface pore diameter, and the elementary analysis were conducted. The results are shown in Table 1.

As in the case of Example 1, the resulting porous membrane had a low average and a low standard deviation of the minor diameter, and the porous membrane exhibited a high water permeability as well as high fractionation performance.

Example 4

The experiment was conducted by repeating the procedure of Example 1 except that the annular slit of the spinneret had an outer diameter of 0.6 mm and an inner diameter of 0.25 mm. The resulting porous membrane in the form of a hollow fiber membrane had an inner diameter of 185 μm and a membrane thickness of 40 μm. The draft ratio was 5.4, and the ratio of the cross-sectional area of the slit to the cross-sectional area of the hollow fiber membrane was 8.4.

The measurement of the water permeability, the measurement of the dextran sieving coefficient, the measurement of the surface pore diameter, and the elementary analysis were conducted. The results are shown in Table 1.

When the annular slit of the spinneret had a larger inner diameter, water permeability was relatively low due to the low porosity. The porous membrane, however, had excellent fractionation performance.

Example 5

The experiment was conducted by repeating the procedure of Example 1 except that the annular slit of the spinneret had an outer diameter of 0.6 mm and an inner diameter of 0.35 mm. The resulting porous membrane in the form of a hollow fiber membrane had an inner diameter of 200 μm and a membrane thickness of 40 μm. The draft ratio was 3.1, and the ratio of the cross-sectional area of the slit to the cross-sectional area of the hollow fiber membrane was 6.2.

The measurement of the water permeability, the measurement of the dextran sieving coefficient, the measurement of the surface pore diameter, and the elementary analysis were conducted. The results are shown in Table 1.

Example 6

The experiment was conducted by repeating the procedure of Example 1 except that the spinning dope solution had a composition of 15% by weight of polysulfone ("Udel" (Registered Trademark) P-3500 manufactured by Solvay), 5% by weight of polyvinylpyrrolidone (K90 manufactured by ISP), 80% by weight of N,N-dimethylacetamide, and 1% by weight of water. The resulting porous membrane in the form of a hollow fiber membrane had an inner diameter of 200 μm and a membrane thickness of 40 μm. The draft ratio was 2.9 and the ratio of the cross-sectional area of the slit to the cross-sectional area of the hollow fiber membrane was 4.9. The measurement of the water permeability, the measurement of the dextran sieving coefficient, the measurement of the surface pore diameter, and the elementary analysis were conducted. The results are shown in Table 1.

Comparative Example 1

The experiment was conducted by repeating the procedure of Example 1 except that the annular slit of the spinneret had an outer diameter of 0.35 mm and an inner diameter of 0.25 mm. The resulting porous membrane in the form of a hollow fiber membrane had an inner diameter of 197 μm and a membrane thickness of 41 μm. The draft ratio was 0.76, and the ratio of the cross-sectional area of the slit to the cross-sectional area of the hollow fiber membrane was 1.5.

The measurement of the water permeability, the measurement of the dextran sieving coefficient, the measurement of the surface pore diameter, and the elementary analysis were conducted. The results are shown in Table 1.

Due to the low draft ratio and the low ratio of the slit cross-sectional area to the cross-sectional area of the hollow fiber membrane, the pore was not sufficiently stretched and the water permeability was relatively low. In addition, due to the high standard deviation of the minor diameter, the porous membrane had low fractionation performance.

Comparative Example 2

The experiment was conducted by repeating the procedure of Comparative Example 1 except that the ejection rate of the dope solution and the ejection rate of the injection liquid were adjusted and the porous membrane in the form of a hollow fiber membrane had an inner diameter of 130 μm and a membrane thickness of 26 μm. The draft ratio was 1.3, and the ratio of the cross-sectional area of the slit to the cross-sectional area of the hollow fiber membrane was 3.1.

The measurement of the water permeability, the measurement of the dextran sieving coefficient, the measurement of the surface pore diameter, and the elementary analysis were conducted. The results are shown in Table 1.

The draft ratio was low since the ejection rate was low despite the high ratio of the slit cross-sectional area to the cross-sectional area of the hollow fiber membrane. Accordingly, the effect of stretching the pores was insufficient, and the porous membrane exhibited high standard deviation of the minor diameter and low fractionation performance.

Comparative Example 3

The experiment was conducted by repeating the procedure of Example 1 except that the spinning dope solution had a composition of 18% by weight of polysulfone ("Udel" (Registered Trademark) P-3500 manufactured by Solvay), 82% by weight of N,N-dimethylacetamide, and 1% by weight of water. The resulting porous membrane in the form of a hollow fiber membrane had an inner diameter of 199 μm and a membrane thickness of 40 μm. The draft ratio was 2.65 and the ratio of the cross-sectional area of the slit to the cross-sectional area of the hollow fiber membrane was 12.9.

The measurement of the water permeability, the measurement of the dextran sieving coefficient, the measurement of the surface pore diameter, and the elementary analysis were conducted. The results are shown in Table 1.

The effect of stretching the pores was insufficient despite the increase of the draft ratio and the cross-sectional area ratio due to the absence of the hydrophilic polymer in the spinning dope solution. Increase in the standard deviation of the minor diameter was thereby invited. Accordingly, the porous membrane had low fractionation performance.

TABLE 1-2

| | Annular slit | | | | | | | | |
|---|---|---|---|---|---|---|---|---|---|
| | Outer diam. (mm) | Inner diam. (mm) | Draft ratio — | Cross-sectional area of the slit/ cross-sectional area of the hollow fiber membrane — | Average of the minor diameter on the inner surface nm | Standard deviation of the minor diameter of the inner surface nm | Porosity of inner surface % | Ratio of the major diameter to the minor diameter of the inner surface — | Standard deviation of the major axis of the inner surface nm |
| Ex. 1 | 0.5 | 0.25 | 2.7 | 4.9 | 10.2 | 3.3 | 5.4 | 3.4 | 17.4 |
| Ex. 2 | 0.73 | 0.23 | 7.6 | 13.0 | 10.9 | 3.4 | 6.4 | 3.6 | 17.7 |
| Ex. 3 | 0.73 | 0.23 | 7.6 | 12.5 | 9.5 | 2.8 | 2.0 | 3.4 | 11.7 |
| Ex. 4 | 0.6 | 0.25 | 5.4 | 8.4 | 10.1 | 3.3 | 4.5 | 3.2 | 16.2 |
| Ex. 5 | 0.6 | 0.35 | 3.1 | 6.2 | 10.8 | 2.3 | 1.1 | 3.0 | 18.6 |
| Ex. 6 | 0.5 | 0.25 | 2.9 | 4.9 | 12.1 | 3.4 | 5.1 | 3.8 | 20.7 |
| Comp. Ex. 1 | 0.35 | 0.25 | 0.76 | 1.5 | 11.1 | 4.2 | 4.9 | 2.9 | 13.9 |
| Comp. Ex. 2 | 0.35 | 0.25 | 1.3 | 3.1 | 12.9 | 4.5 | 2.2 | 2.8 | 15.5 |
| Comp. Ex. 3 | 0.5 | 0.25 | 2.7 | 12.9 | 17.4 | 14.8 | 0.6 | 2.2 | 27.3 |

| | Major diameter to minor diameter ratio of the outer surface — | Average minor diameter on the outer surface μm | Water permeability ml/mmHg/hr/m$^2$ | Cut off molecular weight — | Slope of fractionation curve (absolute value) | Content of hydrophilic polymer wt % |
|---|---|---|---|---|---|---|
| Ex. 1 | 1.9 | 0.4 | 1856 | 73082 | 1.47 | 2.2 |
| Ex. 2 | 2.2 | 0.4 | 2363 | 96774 | 1.50 | 2.3 |
| Ex. 3 | 2.3 | 0.4 | 1943 | 64620 | 1.50 | 2.1 |
| Ex. 4 | 2.5 | 0.3 | 1008 | 30898 | 1.42 | 2.3 |
| Ex. 5 | 3.0 | 0.4 | 557 | 16364 | 1.48 | 2.4 |
| Ex. 6 | 2.7 | 0.4 | 1887 | 75281 | 1.50 | 6.2 |
| Comp. Ex. 1 | 2.0 | 0.4 | 1338 | 55959 | 1.34 | 2.2 |
| Comp. Ex. 2 | 2.2 | 0.1 | 366 | 40030 | 1.06 | 2 |
| Comp. Ex. 3 | *1 | *1 | 470 | 167627 | 0.66 | 0 |

*1 Not determined since the pores could not be confirmed

The invention claimed is:

1. A porous membrane used for blood purification containing a hydrophilic polymer at a content of at least 0.5% by weight and up to 8% by weight wherein pores formed on one surface satisfy the following (A) and (B):

(A) average of ratio of the major diameter to the minor diameter of the pores is at least 3, and (B) average of the minor diameter of the pores is at least 5 nm and up to 20 nm and a standard deviation is up to 4 nm.

2. A porous membrane according to claim 1 wherein pores formed on the other surface satisfy the following (C) and (D):

(C) average of ratio of the major diameter to the minor diameter of the pores is at least 1.5, and (D) average of the minor diameter of the pores is at least 0.2 μm and up to 0.6 μm.

3. A porous membrane according to claim 1 wherein porosity of the surface formed with the pores satisfying the (A) and (B) is at least 1% and up to 10%.

4. A porous membrane according to claim 1 wherein material constituting the main component is an amorphous polymer.

5. A porous membrane according to claim 4 wherein the amorphous polymer is a polysulfone polymer.

6. A porous membrane according to claim 1 wherein the hydrophilic polymer is polyvinylpyrrolidone, polyvinyl alcohol, polyethylene glycol, or a copolymer thereof.

7. A porous membrane according to claim 6 wherein the hydrophilic polymer is polyvinylpyrrolidone or its copolymer.

8. A porous membrane according to claim 1 wherein absolute value of slope of dextran fractionation curve of the porous membrane is at least 1.35.

9. A porous membrane according to claim 1 wherein the membrane is a hollow fiber membrane.

10. A porous membrane according to claim 9 wherein the surface having the pores satisfying the (A) and (B) is the inner surface.

11. A module for blood purification wherein the module accommodates the porous membrane according to claim 1.

12. A method for producing the porous membrane according to claim 1 comprising the steps of ejecting a spinning dope solution containing a hydrophilic polymer from a slit formed in a spinneret, and solidifying the ejected spinning dope solution, after its passage through a dry section, in a coagulation bath to form the porous membrane, wherein cross-sectional area of the slit is 3 to 30 times the cross-sectional area of the solidified porous membrane.

13. A method for producing the porous membrane according to claim 12 wherein the spinning dope solution is in contact with a liquid having a coagulating action also in the dry section, and the liquid contains a poor solvent for the main component constituting the spinning dope solution.

14. A method for producing the porous membrane according to claim 12 wherein concentration of the hydrophilic polymer in the spinning dope solution is at least 10% by weight and up to 70% by weight of the concentration of the main component polymer constituting the spinning dope solution.

* * * * *